US008784352B2

(12) United States Patent
Huttner

(10) Patent No.: US 8,784,352 B2
(45) Date of Patent: Jul. 22, 2014

(54) DEVICE AND METHOD FOR PREVENTION OF SWIMMER'S EAR

(75) Inventor: James J. Huttner, Sylvania, OH (US)

(73) Assignee: Bionix Development Corporation, Toledo, OH (US)

( * ) Notice: Subject to any disclaimer, the term of this patent is extended or adjusted under 35 U.S.C. 154(b) by 352 days.

(21) Appl. No.: 12/785,519

(22) Filed: May 24, 2010

(65) Prior Publication Data

US 2010/0305540 A1 Dec. 2, 2010

Related U.S. Application Data

(60) Provisional application No. 61/181,021, filed on May 26, 2009.

(51) Int. Cl.
*A61M 35/00* (2006.01)
*A61F 13/20* (2006.01)

(52) U.S. Cl.
USPC .............................................. 604/1; 604/11

(58) Field of Classification Search
USPC ....................................... 604/11, 1
See application file for complete search history.

(56) References Cited

U.S. PATENT DOCUMENTS

| 3,818,911 | A | * | 6/1974 | Fournier ........................... 604/1 |
| 5,417,224 | A | * | 5/1995 | Petrus et al. ................... 128/833 |
| 5,584,827 | A | * | 12/1996 | Korteweg et al. ............. 604/369 |
| 6,099,952 | A | * | 8/2000 | Cercone ..................... 428/308.4 |
| 6,725,568 | B2 | | 4/2004 | Gronke |
| 8,122,892 | B2 | * | 2/2012 | Johnson et al. ............... 128/865 |

OTHER PUBLICATIONS

Eyetec, "Eye Spears", published before May 26, 2009.
QOSINA, "Dual Pointed Sponge", published before May 26, 2009.
QOSINA, "Tightly Wound Point Tips Swab . . . ", published before May 26, 2009.

* cited by examiner

*Primary Examiner* — Jacqueline F. Stephens
(74) *Attorney, Agent, or Firm* — Marshall & Melhorn, LLC

(57) ABSTRACT

A device and method for removing residual water from the external ear canal of an individual comprise using a portion of dry, pre-compressed, absorbent sponge material that is die-cut or otherwise fashioned to have a bluntly pointed tip on at least one end. The bluntly pointed tip is placed into the external ear canal of an individual, and this bluntly pointed tip is held in place until there is visible and/or tactile evidence of water absorption by the sponge material, as indicated by swelling and/or softening of the bluntly pointed tip. These steps may be repeated as necessary to remove further residual water from the individual's ear canal.

15 Claims, 2 Drawing Sheets

DEVICE AND METHOD FOR PREVENTION OF SWIMMER'S EAR

CROSS-REFERENCE TO RELATED APPLICATIONS

This application is claiming the benefit, under 35 U.S.C. §119(e), of the provisional application filed May 26, 2009 under 35 U.S.C. §111(b), which was granted Ser. No. 61/181,021. This provisional application is hereby incorporated by reference in its entirety.

BACKGROUND OF THE INVENTION

Swimmer's ear, also known as external otitis, is a common and painful condition of the external ear canal that results when water from swimming or similar activities remains in the ear canal for a prolonged period of time after the activity.

In the normal ear canal, the skin of the canal is dry and provides an intact barrier. Along with the usual acidic pH of the ear canal, this keeps the bacteria that colonize the ear canal from invading the tissue and causing infection. After activities such as swimming or diving, water that enters the ear canal can remain there, held in place by capillary action and surface tension. This causes the normally dry skin of the ear canal to become over hydrated, increasing its permeability and making it more susceptible to infection. The resulting bacterial infection of the ear canal wall is an intensely painful condition known as external otitis, or swimmer's ear.

Although external otitis can be treated by the application of topical antibiotic drops, it is preferable to try to prevent the condition from occurring. Since the causative factor is residual water in the ear canal, removing that water as soon as possible after swimming is a simple and effective method of preventing the cascade of events that can lead to swimmer's ear. Several methods are effective in achieving this result.

First, many devices exist to try to prevent water from entering the ear canal during swimming or similar activities. These include ear plugs of various types and waterproof headbands. Although effective, these devices fail when they fall out of the ear canal or are improperly fitted or positioned. Also, small children often remove these devices when away from the supervising parent. In these cases the barrier to water entry is gone, and water freely enters the ear canal.

A second method is to remove the residual water in the ear canal by mechanical means, using a cotton swab or tissue to absorb the water from the canal. Although effective, the significant drawback is the relatively low absorbent volume of such products, and the potential for pushing wax and debris further into the ear canal, resulting in other ear problems (impacted wax, etc.). Bionix Development Corporation introduced a device using this technique for sale in 2002, using a swab having absorbent polyurethane foam to remove residual water from the ear canal. Although the expanded foam used had a greater water absorptive capacity than cotton or tissue, it still suffered the drawbacks of these devices, as described above.

Another method uses a battery powered blower to dry the ear canal (DryEar™ U.S. Pat. No. 6,725,568). This method is cumbersome and time consuming, and such devices are expensive and prone to running out of power. Also, using the same device for several individuals risks cross-contamination from person to person.

Yet another method uses a solution of glycerine and alcohol (available as commercial ear drops) instilled into the ear canal. The alcohol decreases the surface tension of the water, allowing it to flow from the ear more easily. Acetic acid is often also added to the drops produce an acidic pH. It is still important to remove the fluid from the ear canal after instillation of the drops. Also, the drops can be irritating and difficult to use in small children.

BRIEF SUMMARY OF THE INVENTION

The invention is a device and method for removing residual water from the external ear canal of an individual, comprising using a portion of dry, pre-compressed absorbent sponge material that is die-cut or otherwise fashioned to have a bluntly pointed tip on at least one end. The bluntly pointed tip is placed into the external ear canal of an individual, and this bluntly pointed tip is held in place until there is visible and/or tactile evidence of water absorption by the sponge material, as indicated by swelling and/or softening of the bluntly pointed tip. These steps may be repeated as necessary to remove further residual water from the individual's ear canal.

Non-compressed sponges exist in configurations similar to that described herein. However, these sponges are soft and flexible prior to use, and as such lack the ability to be introduced into the small opening of the external ear canal. Also, they lack the absorbent qualities of the dry, pre-compressed sponge material, making them poor choices for this application.

Double ended swabs exist, and have been used in the consumer marketplace for removal of water and/or debris from the external ear canal. Known most commonly by the trademark "Q-Tips," many companies manufacture similar swabs. However, these swabs are comprised of tightly wound cotton or polyester fibers on the end of a plastic or paper stick. Such materials have limited ability to absorb and retain water as compared to dry, pre-compressed sponge material, and as such are poor choices for removing the significant quantity of water that may be found in the external ear canal after swimming or bathing.

Compressed sponges are well known, and devices made from them are widely used in medical and consumer applications. Of the currently manufactured devices, those having generally pointed ends consist of compressed sponge tips affixed to plastic handles, and are used for eye surgery and similar applications. There are no dry, pre-compressed sponge devices indicated for use in the ear, and specifically none proposed previously for removal of water from the external ear canal after swimming or bathing.

BRIEF DESCRIPTION OF THE DRAWINGS

The advantages of the invention will become readily apparent to those skilled in the art from the following detailed description of various embodiments when considered in the light of the accompanying drawings, in which.

DETAILED DESCRIPTION OF THE INVENTION

It is to be understood that the specific devices and processes illustrated in the attached drawings and described in the following description are simply exemplary embodiments of the inventive concepts defined in the appended claims. Hence, specific dimensions and other physical characteristics relating to the embodiments disclosed herein should not be considered as limiting, unless the claims expressly state otherwise.

The invention is a simple and effective method of removing residual water from the ear canal after swimming or similar activities. It uses a dry, pre-compressed sponge material that is shaped to safely enter the ear canal. The dry, pre-compressed sponge material has a very large water absorbing capacity. This material, when in contact with water, tends to absorb the water, expanding in volume and softening. As a result, once in the ear canal, the dry, pre-compressed sponge material begins to absorb water. In doing so it swells and softens, preventing it from being pushed further into the ear canal. After safely absorbing the water from the ear canal, the sponge is withdrawn and discarded, preventing cross-contamination to other individuals.

The invention utilizes a dry, pre-compressed sponge material that is die-cut or otherwise fashioned to have a bluntly pointed tip designed to enter the ear canal of an individual, child or adult. In the preferred embodiment, there is a similar tip on the other end of the device. The size of the device is such that the blunted tip can safely enter the ear canal, yet has sufficient absorptive capacity to allow effective removal of residual water in the external ear canal. The user typically holds the device by its middle portion, and is able to reverse the device to allow removal of water from the swimmer's other ear canal. The sponge material is formed of a suitably absorbent material, such as a polyvinyl alcohol material, a polyester material, a low-density polyether material, a polyvinyl acetal material, or the like, or a cellulosic material, that has been compressed. The sponge material is most preferably cellulosic in composition.

Figure 1:
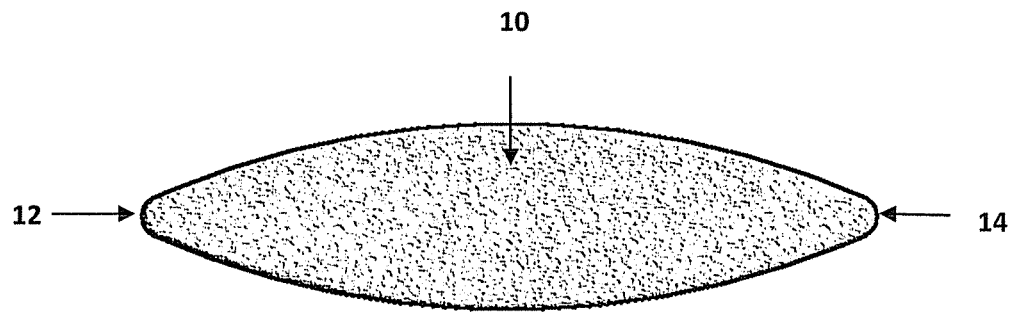
FIG. 1 is a top view of an embodiment of a device for use in accordance with the invention.
Figure 2:
FIG. 2 is a side view of the embodiment of the device shown in FIG. 1.
Figure 3:
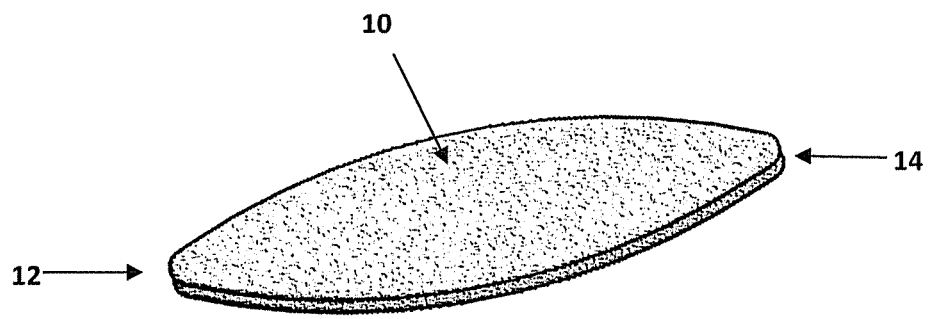
FIG. 3 is a perspective view of the embodiment of the device shown in FIG. 1.

A preferred device for use in accordance with the invention is illustrated in FIGS. 1 through 3. FIG. 1 is a top view of the device with the first and second ends 12 and 14 shown. The main body 10 is shown as textured to indicate the dry, pre-compressed sponge material of its makeup.

FIG. 2 shows a side view of the preferred device, again with the first and second ends 12 and 14 shown, and texture to indicate the dry, pre-compressed sponge material of its makeup.

FIG. 3 shows a perspective view of the invention, again with the first and second ends 12 and 14 and the main body 10 shown as textured to indicate the dry, pre-compressed sponge material of its makeup.

Figure 4:
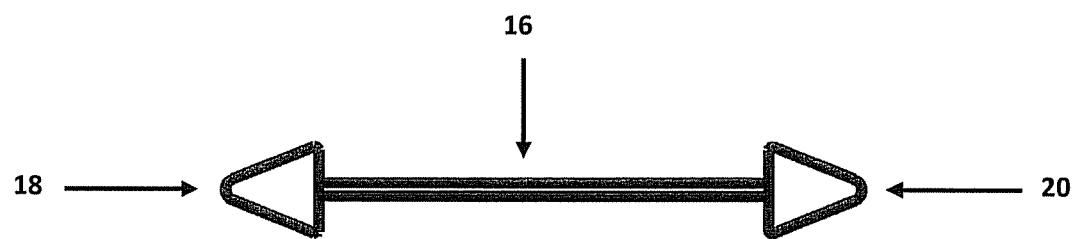
FIG. 4 is a top view of an alternate embodiment of a device for use in accordance with the invention.

An alternative device for use in accordance with the invention is illustrated somewhat schematically in FIG. 4. In FIG. 4, a first end 18 and a second end 20 of the device shaped into a generally triangular form. The ends 18 and 20 are composed of dry, pre-compressed foam even though the ends 18 and 20 are not shown as textured due to the somewhat schematic nature of this figure. The ends 18 and 20 are joined to each other by a swab-stick 16 that may be comprised of plastic, paper, wood, or the like, that is relatively rigid as compared to the ends 18 and 20.

Figure 5:
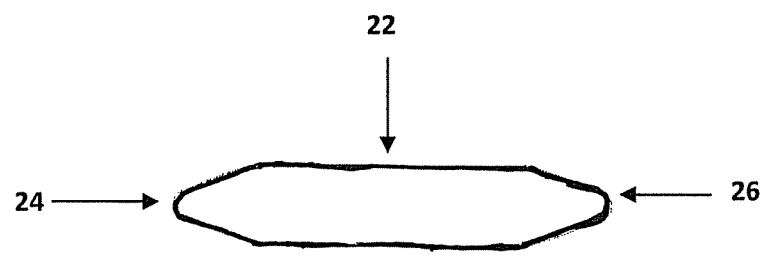
FIG. 5 is a top view of a further embodiment of a device for use in accordance with the invention.

A further embodiment of the device is shown in FIG. 5. In the embodiment of FIG. 5, the first end 24 and second end 26 have generally rounded tips, and the main body 22 has a generally rectangular configuration. Although the device of FIG. 5 is not shown textured, it is again assumed that the entire device shown in FIG. 5 is comprised of dry, pre-compressed foam material.

Other configurations of the current invention are also possible. It is assumed that one skilled in the art can infer alterations in the size and shape of the preferred embodiment that would still be functional and user friendly.

In use, the swimmer or parent takes one double-ended device from the package. Holding the device by its middle portion, the user inserts the bluntly pointed tip into the swimmer's ear canal and holds it there until the residual water in the ear canal has been absorbed, indicated by the sponge material swelling and softening. The device is reversed, and the other bluntly pointed tip can be used to remove water from the swimmer's other ear, or to remove even more water from the same ear, if needed. After use, the device is discarded. It cannot be reused, and cannot transfer infection to other individuals.

In accordance with the provisions of the patent statutes, the invention has been described in what is considered to represent its preferred embodiments. However, it should be noted that the invention could be practiced otherwise than as specifically illustrated and described without departing from its spirit or scope. As an example, it will be appreciated that, in those embodiments in which the apparatus includes a plurality of projections, the size and shape of the projections may vary considerably.

What is claimed is:

1. A method for removing residual water from the external ear canal of an individual, comprising the steps of:
   a. providing a device having a bluntly pointed tip on at least one end, wherein at least the bluntly pointed tip is comprised of a dry, pre-compressed, absorbent sponge material of a size and shape able to fit into the proximal portion of the external ear canal;
   b. placing said bluntly pointed tip into the external ear canal of an individual, said bluntly pointed tip retaining its size and shape until coming into contact with water in the external ear canal;
   c. holding said bluntly pointed tip in place until there is visible and/or tactile evidence of water absorption by the sponge material, as indicated by swelling and softening of said bluntly pointed tip; and
   d. withdrawing said bluntly pointed tip from the external ear canal of the individual.

2. The method of 1, wherein the sponge material is comprised of a cellulosic material.

3. The method of 1, wherein the sponge material is comprised of a polyvinyl alcohol material.

4. The method of 1, wherein the sponge material is comprised of a polyester material.

5. The method of 1, wherein the sponge material is comprised of a low-density polyether material.

6. The method of 1, wherein the sponge material is comprised of a polyvinyl acetal material.

7. The method of 1, wherein the device comprises a bluntly pointed tip on both ends of the device, wherein at least both of the bluntly pointed tips is comprised of dry, pre-compressed absorbent sponge material.

8. The method claim 1, wherein steps "a" through "d" are repeated one or more times as necessary to remove further residual water from the individual's ear canal.

9. A device for removing water or other liquid from the external ear canal of a person or animal, comprising:
   a. a portion of dry, pre-compressed, absorbent sponge material that is die-cut or otherwise fashioned to have a bluntly pointed tip on at least one end,
   b. said bluntly pointed tip being of a size and shape able to fit into the proximal portion of the external ear canal, and
   c. said dry, pre-compressed, absorbent sponge material being able to absorb and hold water as evidenced by visible swelling and tactile softening of the sponge material only after contact with water in the ear canal.

10. The device of 9, wherein the dry, pre-compressed absorbent sponge material is double ended in that it has a bluntly pointed tip on both ends of the device.

11. The device of 9, wherein the sponge material is comprised of a cellulosic material.

12. The device of 9, wherein the sponge material is comprised of a polyvinyl alcohol material.

13. The device of 9, wherein the sponge material is comprised of a polyester material.

14. The device of 9, wherein the sponge material is comprised of a low-density polyether material.

15. The device of 9, wherein the sponge material is comprised of a polyvinyl acetal material.

* * * * *